(12) United States Patent
Pozueta Romero et al.

(10) Patent No.: US 8,841,513 B2
(45) Date of Patent: Sep. 23, 2014

(54) PROCEDURE FOR PRODUCING TRANSGENIC PLANTS PROVIDING HIGH STARCH CONTENT AND YIELD AND HIGH AMYLOSE/AMYLOPECTIN BALANCE

(75) Inventors: Francisco Javier Pozueta Romero, Pamplona (ES); Miren Edurne Baroja Fernández, Pamplona (ES); Francisco José Muñoz Pérez, Pamplona (ES); Nora Alonso Casajús, Pamplona (ES)

(73) Assignee: Idén Biotechnology, S.L., Pamplona (ES)

( * ) Notice: Subject to any disclaimer, the term of this patent is extended or adjusted under 35 U.S.C. 154(b) by 464 days.

(21) Appl. No.: 13/063,293

(22) PCT Filed: Sep. 10, 2009

(86) PCT No.: PCT/ES2009/070376
§ 371 (c)(1),
(2), (4) Date: Jun. 2, 2011

(87) PCT Pub. No.: WO2010/029206
PCT Pub. Date: Mar. 18, 2010

(65) Prior Publication Data
US 2011/0271401 A1    Nov. 3, 2011

(30) Foreign Application Priority Data

Sep. 12, 2008   (ES) .................................. 200802608

(51) Int. Cl.
*C12N 15/00*   (2006.01)
*C12N 15/82*   (2006.01)
*A01H 5/00*    (2006.01)
*C12N 9/10*    (2006.01)

(52) U.S. Cl.
CPC .................................. *C12N 15/8245* (2013.01); *C12N 9/1051* (2013.01)
USPC .......................... 800/284; 435/320.1; 800/298

(58) Field of Classification Search
None
See application file for complete search history.

(56) References Cited

PUBLICATIONS

Dauvillee et al, 2006, The Plant J., 48:274-285.*
Slattery et al, 2000, Trends in Plant Sci., 5:291-298.*
Schupp N. et al. "The relation of starch phosphorylases to starch metabolism in wheat" Plant and Cell Physiology, vol. 45(10), pp. 1471-1484, 2004.
Dauvillée D. et al. Plastidial phosphorylase is required for normal starch synthesis in *Chlamydomonas reinhardtii* The Plant Journal, vol. 48, pp. 274-285, 2006.
Satoh H. et al. "Mutation of the plastidial α-glucan phosphorylase gene in rice affects the synthesis and structure of starch in the endosperm" The Plant Cell, vol. 20, pp. 1833-1849, Jul. 2008.
Curtis L. et al. "The complexities of starch biosynthesis in cereal indosperms" Current Opinion in Biotechnology, vol. 19, pp. 160-165, Apr. 2008.

* cited by examiner

*Primary Examiner* — Ashwin Mehta
*Assistant Examiner* — Jason Deveau Rosen
(74) *Attorney, Agent, or Firm* — Tristan A. Fuierer; Andrew D. Gerschutz; Moore & Van Allen, PLLC

(57) ABSTRACT

A process for the production of transgenic plants that have a high starch content and yield and a high amylose/amylopectin ratio. The alpha-1,4-glucan phosphorylases (GPs) catalyze the reversible cutting of bonds α-1,4 of the non-reducing ends of homopolysaccharides with at least 5 glucose molecules such as starch, maltodextrin and glycogen, leading to production of glucose-1-phosphate. The GPs in bacteria and animal cells are responsible for the breakdown of glycogen. Although the increase in GP activity leads to a reduction in intracellular levels of glycogen in bacteria and animal cells, this invention discloses the production of plants that have high starch levels and yields and high amylose/amylopectin ratio, as result of the expression of genes coding for GPs.

12 Claims, 13 Drawing Sheets

PROCEDURE FOR PRODUCING TRANSGENIC PLANTS PROVIDING HIGH STARCH CONTENT AND YIELD AND HIGH AMYLOSE/AMYLOPECTIN BALANCE

CROSS-REFERENCE TO RELATED APPLICATIONS

This application is filed under the provisions of 35 U.S.C. §371 and claims the priority of International Patent Application No. PCT/ES2009/070376 filed on 10 Sep. 2009 entitled "Procedure for Producing Transgenic Plants Providing High Starch Content and Yield and High Amylose/Amylopectic Balance" in the name of Francisco Javier POZUETA ROMERO, et al., which claims priority to Spanish Patent Application No. P200802608 filed on 12 Sep. 2008, both of which are hereby incorporated by reference herein in their entirety.

FIELD OF THE INVENTION

The present invention is encompassed within the field of genetic engineering and plant physiology. Specifically, the invention comprises a method for producing transgenic plants with high starch levels and a high amylose/amylopectin ratio, the vectors used to transform cells, the transformed cells themselves, the transgenic plants obtained by this process and their uses.

STATE OF THE PRIOR ART

Both starch in plants and glycogen in bacteria and animals are branched homopolymers of glucose molecules linked by covalent bonds of type $\alpha$-1,4 and $\alpha$-1,6. These polymers are important carbohydrate and energy storage forms. In plants, starch is synthesized in the plastid, it accumulates in large amounts in organs such as seeds (wheat, barley, corn, peas, etc.) and tubers (potato and sweet potato among others) and is a fundamental constituent of human diet. On the other hand, starch is frequently used in the paper, cosmetics, pharmaceutical and food industries, as well as basic raw material for the manufacture of biodegradable plastics, paints with low environmental impact and bioethanol. Numerous starch applications are based primarily on the balance of amylose and amylopectin, which determines the structure of the starch granule and its viscosity in aqueous suspensions.

ADPG is the universal precursor molecule for the biosynthesis of starch and glycogen in plants and bacteria, respectively. It is widely assumed that the production of this nucleotide sugar is exclusively controlled by the enzyme ADPG pyrophosphorylase (AGPase) (EC 2.7.7.27) (1-4). However, there is evidence to show that sucrose synthase (EC 2.4.1.13) (UDP-glucose:D-fructose-2-glucosyl transferase) is involved in the synthesis of ADPG necessary for starch biosynthesis (5-9). Where ADPG degradation mechanisms are concerned, there are ADPG-hydrolyzing enzymes both in plants (10-13) and in bacteria (14,15).

In plants, starch degradation is controlled by hydrolytic reactions catalyzed by $\alpha$-amylase, $\beta$-amylase and $\alpha$-glucosidase (16,17). By contrast, in animals, bacteria and yeasts it is the alpha-1,4-glucan phosphorylase (GP) (EC 2.4.1.1) that controls the degradation of the glycogen molecule in vivo (18-22). GPs catalyze the reversible cutting of $\alpha$-1,4 bonds of the nonreducing polyglucan ends such as starch, maltodextrin and glycogen, leading to the production of glucose-1-phosphate (G1P). The nucleotide sequences of animal, plant or bacteria origin, which code for enzymes with GPs activity, are conserved sequences.

Plants have intra- and extra-plastidial GPs. Unlike what happens in bacteria, yeast and animals, so far the role of plant GPs is unknown, especially those that are intraplastidial. Taking into account the reversibility of the GPs, it is possible that their role in starch metabolism depends on the balance Pi/G1P (21). Thus, the existing high Pi/G1P balance in plant cells strongly indicates that the plastidial GP is not involved in starch synthesis, reinforcing the theory that starch synthesis takes place exclusively through processes dependent on the production of ADPG.

There is evidence to suggest the possible involvement of plastidial GPs in starch degradation in leaves of *Phaseoulus vulgaris* and *Arabidopsis thaliana* (23). On the other hand, it has been suggested that plastidial GPs have functions related to abiotic stress, flowering and seed growth (24-27). The discussion about the biological function of the plastidial GPs in plants is further complicated when taking into account that STA4 mutants of the alga *Chlamydomonas reinhardtii* deficient in plastidial GP, have reduced levels of starch, which suggests that the plastidial GP is not involved in the starch degradation in *C. reinhardtii* (28). On the other hand, there are studies showing that plastidial GPs are not involved in starch degradation in vascular plants such as potato and wheat (29, 30). Adding more confusion to the debate about the possible involvement of the plastidial GP in starch degradation, some studies have shown a positive correlation.

There are works that describe the production and characterization of plants with low GP activity (24). These plants accumulate normal levels of starch. On the other hand, there is a work describing the overexpression of the *E. coli.* glgP gene coding for GP, results in bacteria with reduced or zero levels of glycogen (22). Finally, there are works describing that the overexpression of genes encoding mammalian GP results in human cells with reduced levels of glycogen (18). The prior art offers no clear relationship between the plant GP enzyme and its specific function. Indeed, so far there are no known publications on the production and/or characterization of higher plant species with high GP activity.

The present invention is focused precisely on this last point in describing vascular transgenic plants with high GP activity (both cytosolic and plastidial) characterized by expressing genes coding for proteins/enzymes with GP activity getting a high GP activity (both cytosolic and plastidial) and consequently a high starch level and performance and a high amylose/amylopectin balance. Another important aspect to consider is that the present invention shows that the expression of genes coding for GP enzymes, and therefore increased GP activity, results in a starch content increase.

Thus, the present invention breaks the prejudice established in the state of the art for animal, bacteria and yeast GP activity, which defines that the GP activity tends to cut bonds $\alpha$-1,4 of glucose polymers leading to G1P. It also shows that the bacterial GP promotes the synthesis of starch in transgenic plants expressing the gene coding for this enzyme.

Thus, the object of the invention is the production of plants with high starch content and yield and a high amylose/amylopectin balance as a result of the increase in GP activity (both in the cytosol and in the plastid) to express genes encoding for proteins with GP activity.

DESCRIPTION OF THE INVENTION

Brief Description of the Invention

As discussed above, the object of the invention is the production of transgenic plants with high starch content and yield and a high amylose/amylopectin balance as a result of the increase in GP activity (both in the cytosol and in the plastid) to express genes encoding for proteins with high GP activity. For the purposes of this invention, the following terms are noted:

Cell: the smallest unit (morphological and functional) of all living beings, capable of acting autonomously. Bacterial and plant cells are particularly interesting for the present invention.

Cytoplasm: a liquid solution that makes up the intracellular medium.

Plastid: organelle characteristic of plant cells. It is responsible for photosynthesis in photosynthetic eukaryotic organisms.

Genetic Vectors: "vehicle" used to transfer exogenous genetic material to the interior of a cell. Any vector known in the art may be used in the present invention. However in the present invention *Agrobacterium tumefaciens* was preferably used.

Homologous sequences: virtually identical DNA nucleotide sequences, including base pairing which can occur under strict conditions.

Ectopic expression: ectopic expression of a gene refers to when its product is expressed in a place where it normally does not.

Transgenic plant: a plant whose genome has been genetically engineered with the aim of achieving biological characteristics different from those of the wild plant (as is the case of the present invention).

High activity of the GP enzyme: this refers to high GP enzyme activity when such activity is at least 5 times greater than that existing in wild plants.

High starch content: as used herein, this expression is directly referred to a statistically significant value, higher than the values observed in control plants. FIG. 7 shows that the average starch content in tubers of the wild plants analyzed (CR1 and CR2) is approximately 290 μmoles glucose/g (fresh weight), with a margin of variation of 10%. Therefore a "high content in Amidon" may be considered as that which exceeds, by at least 20%, the value of 290 μmoles of glucose/g (fresh weight). This value is exceeded in the present invention obtaining transgenic tubers which accumulate starch quantities of 400 μmoles glucose/g (fresh weight) minimum.

High amylose/amylopectin ratio: as noted in FIG. 9, the amylose/amylopectin ratio, expressed as a percentage of amylase, in the tubers of wild plants (CR) analyzed is approximately 22.5% with a margin of error of 2.5% (which constitutes 10% of the average value observed in CR). It is considered that there is a high amylose/amylopectin ratio when the amylose percentage value of transgenic plants analyzed is at least 10% greater than the amylose percentage value in the corresponding wild plant (in this case, tubers with an amylose/amylopectin ratio greater than 25% are considered rich in amylose).

DETAILED DESCRIPTION OF THE INVENTION

Obtaining and Purifying Active Recombinant GP

Figure 1:
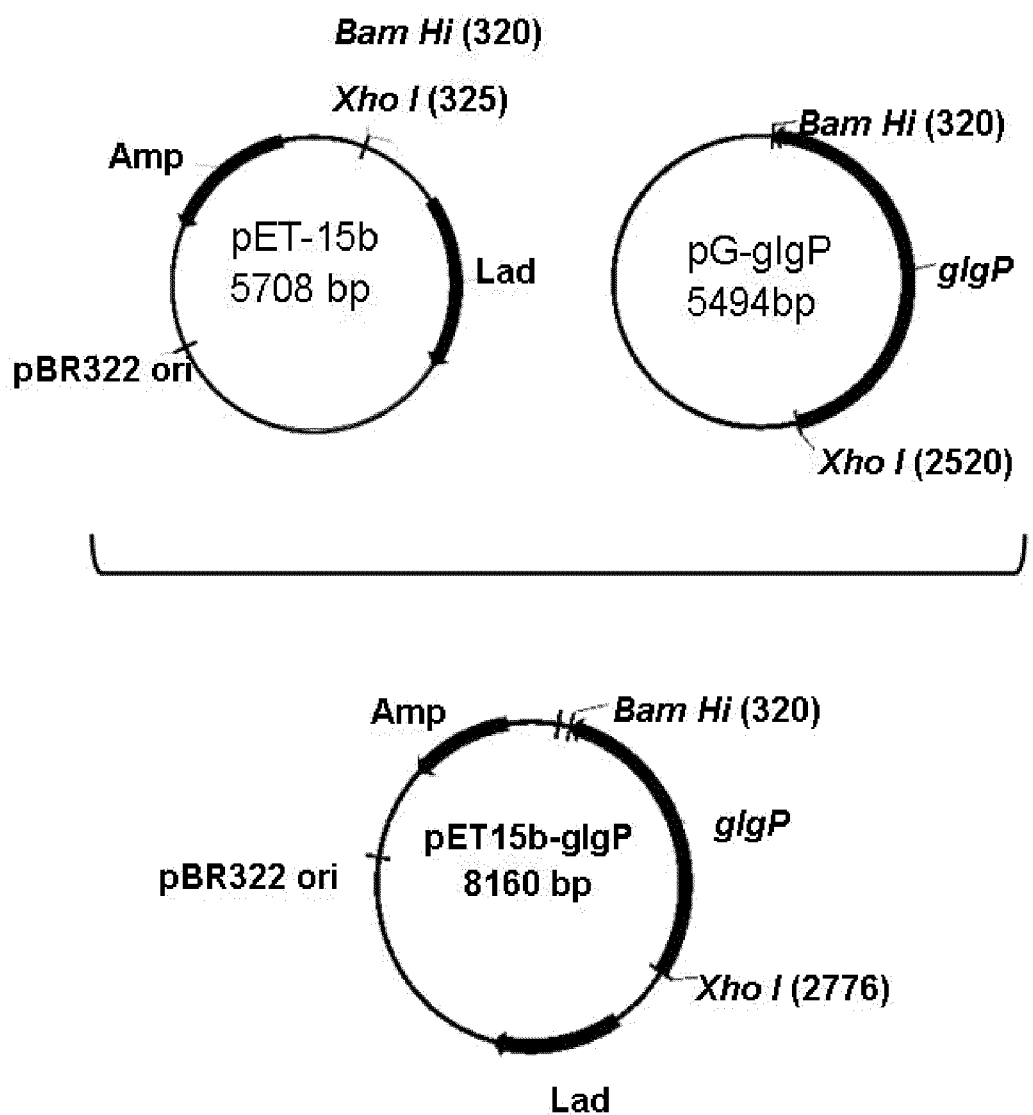
FIG. 1: Stages of construction of expression plasmid pET15b-glgP.
Figure 2A:
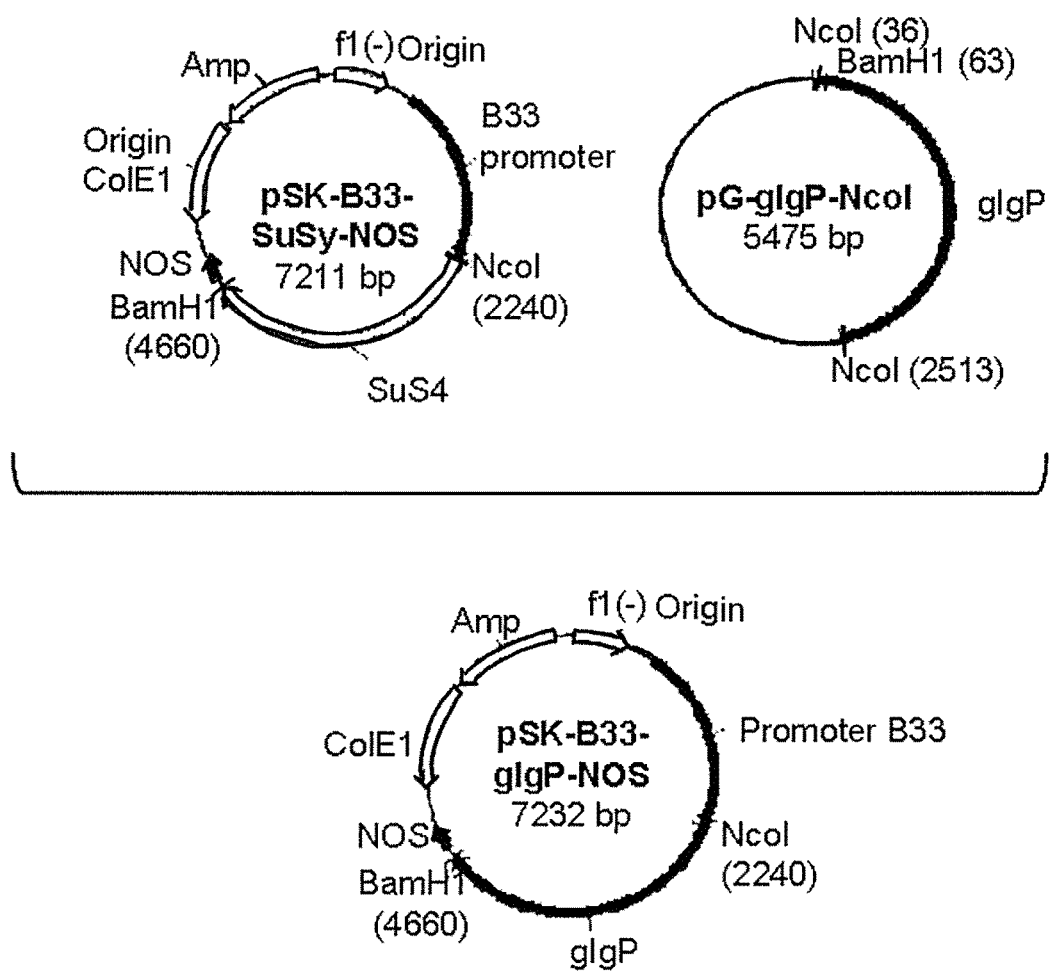
FIG. 2A: Production of the plasmid pSK-B33-glgP-NOS using plasmids pG-glgP-NcoI and pSK-B33-SuSy-NOS.
Figure 2B:
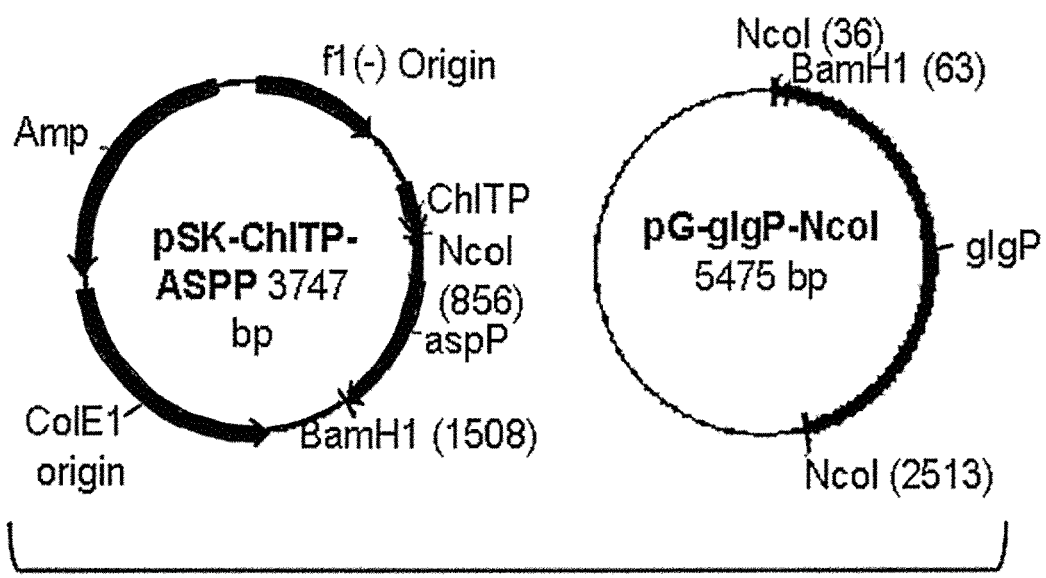
FIG. 2B: Production of the plasmid pSK-Ch1TP-glgP using the plasmids pG-glgPNcoI and pSK-Ch1TP-ASPP.
Figure 2B:
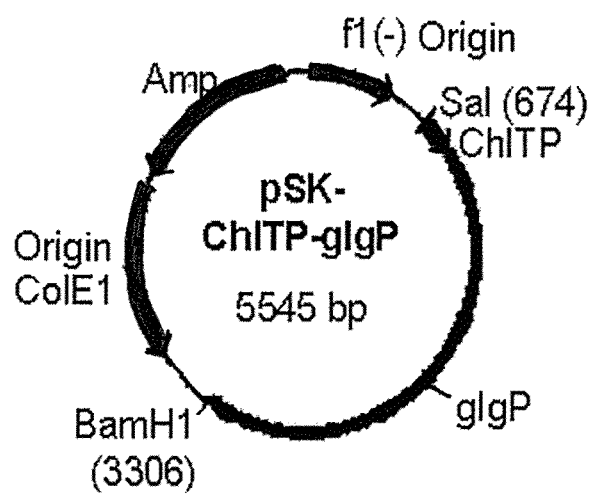
Figure 2C:
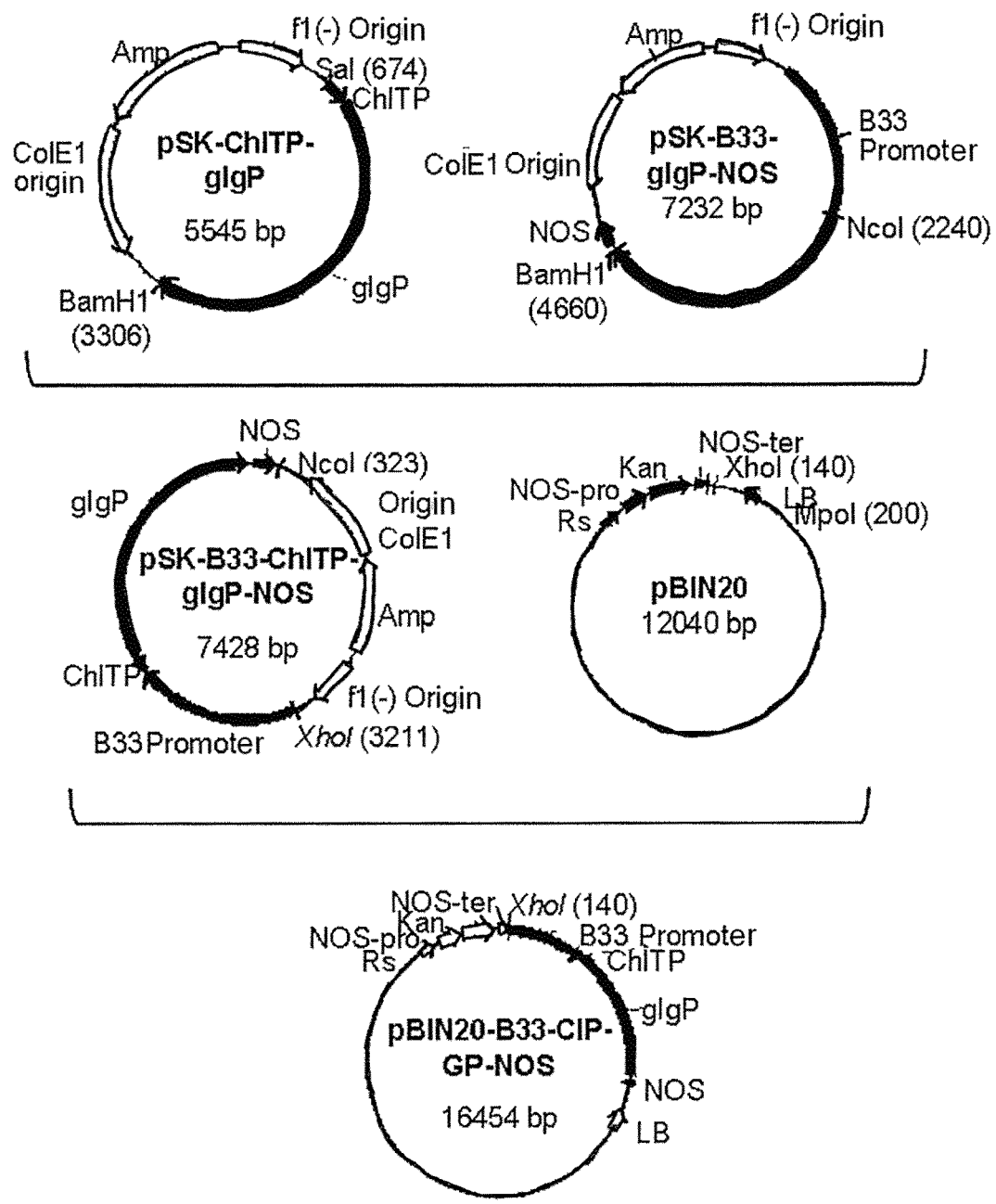
FIG. 2C: Production of the plasmid pBIN20-B33-C1P-GP-NOS using the plasmids pSK-Ch1TP-glgP pSK-B33-glgP-NOS and pBIN20.

The nucleotide sequence of *Escherichia coli* glgP (22) being known, two specific primers (SEQ ID NO: 1 and SEQ ID NO: 2) were created, corresponding to the gene ends 5' and 3'. By using these primers, a DNA fragment of approximately 2460 base pair was amplified by conventional PCR methods, from genomic DNA of *E. coli*. This DNA fragment was introduced into the plasmid pGemT-easy (Promega) resulting in the pG-glgP construction (FIG. 1) which was amplified in XL1 Blue host bacteria. PG-glgP was digested with restriction enzymes XhoI and BamHI. The released fragment (containing glgP) was cloned into the same restriction sites of the expression plasmid pET-15b (+) (Novagen). The resulting plasmid designated by the name of pET15b-glgP (FIG. 1) was introduced by electroporation into the strain *E. coli* BL21 (DE3) C43 (Novagen) with deposit number CECT 7071. glgP expression was effected by adding 1 mM isopropyl-β-D-thiogalactopyranoside (IPTG) in 100 ml of cell culture grown at 37° C. After six hours of induced culturing bacteria were harvested and resuspended in 4 ml of binding buffer (Novagen, His-bind purification kits), were sonicated and centrifuged at 40,000 g for twenty minutes. The supernatant containing the recombinant GP with a histidine tag at the N-terminal was passed through an affinity column of the Novagen "His-bind" protein purification kit. Following the instructions of the kit the GP was eluted with 6 ml recommended elution buffer, which included 200 mM of imidazole instead of 1 molar. After elution the protein was quickly subjected to dialysis to remove any trace of imidazole that could irreversibly inactivate the GP.

Determination of Soluble Sugars and Starch Content

Soluble sugars were extracted using the techniques described in the scientific literature (34, 35). Sucrose, maltose, maltotriose, maltotetraose, maltopentaose, maltohexaose, maltoheptaose, fructose and glucose were determined using a DIONEX automated ion chromatograph fitted to a PA10 CarboPac column, an ED50 electrochemical detector, a GP50 E1 gradient pump and an E01 organizer of the eluents (22). ADPG was determined using a HPLC Waters system fitted to a Partisil-10-SAX column (10). Starch, glycogen and amylopectin were measured using commercial kits described in the literature (36). The amylose/amylopectin ratio was determined using the spectrophotometric method described in the literature (36).

Identification of the Product with GP Enzyme Activity

The GP enzymatic product was identified by the following functional pattern:

It is an alpha-1,4-glucan phosphorylase (EC 2.4.1.1). Very often, this enzyme catalyzes the reversible phosphorolysis cut of bonds α-1,4 of the non-reducing ends of homopolysaccharides of glucose molecules (branched or not) covalently bonded through links α-1, 4 and α-1,6 such as maltodextrins, starch and glycogen, leading to the production of G1P.

Obtaining Specific GP *E. coli* Polyclonal Antibodies

Two milligrams of purified recombinant *E. coli* GP were separated on SDS-PAGE. After being eluted, purified recombinant GP was mixed with Freund's complete adjuvant (in a 50/50 ratio) and was then aliquoted into three equal fractions, each of which was injected into a rabbit in two-week periods. After about two months after the first injection, blood serum was extracted from the rabbit containing specific to *E. coli* GP polyclonal antibodies.

Identification of the Product by the Western Blot Technique

Crude extracts of wild plants and tubers of transgenic plants expressing the glgP gene coding for *E. coli* GP were separated on SDS-PAGE. They were subsequently transferred to nitrocellulose membranes and the *E. coli* GP was detected using the specific antibody anti GP of *E. coli* according to the methodology described in the literature (37).

Obtaining Transgenic Plants Expressing *E. coli* glgP a. Potato Plants with High GP Activity in Amyloplasts of Tubers The plasmid pG-glgP-NcoI (identical to pG-glgP, except it has an NcoI site at the ATG translation initiation codon) was digested with enzymes NcoI and BamHI. The fragment released was cloned into NcoI and BamHI sites of pSK-B33-SuSy-NOS (B33 is the promoter region of the gene encoding for the patatin whose expression is specific to tubers) (38) giving rise to the plasmid pSK-B33-glgP-NOS (FIG. 2).

For the production of a gene construction that encodes for the GP of *E. coli* located in the plastid, pG-glgP-NcoI was digested with NcoI and BamHI. The fragment released was cloned between NcoI and BamHI sites of the plasmid pSK-Ch1TP-ASPP containing the region of the gene encoding for the chloroplast transit peptide of the protein P541 (39), resulting in the plasmid pSK-Ch1TP-glgP (FIG. 2).

To produce a construction that encodes for the GP of *E. coli* that specifically accumulates in amyloplasts of potato tubers, pSK-Ch1TP-glgP was digested successively with SalI, T4-DNA polymerase and BamHI. The fragment released was cloned into pSK-B33-glgP-NOS after having been digested successively with NcoI, T4 DNA polymerase and BamHI, resulting in the plasmid pSK-B33-Ch1TP-glgP-NOS (FIG. 2).

For the production of a binary plasmid containing the gene construction B33-Ch1TP-NOS-glgP necessary to transform plants via *Agrobacterium tumefaciens*, psK-B33-Ch1TP-glgP-NOS was digested sequentially with NotI, T4 DNA polymerase and XhoI. The fragment released was cloned into the binary plasmid pBIN20 (40) which had previously been sequentially digested with HpaI, T4 DNA polymerase and XhoI, resulting in the plasmid pBIN20-B33-C1P-GP-NOS (FIG. 2). PBIN20-B33-C1P-GP-NOS was introduced by electroporation into different strains of *A. tumefaciens* necessary to transform species such as potato, *Arabidopsis thaliana*, tomato, tobacco, corn and rice (such as the strain C58:GV2260, with deposit number CECT 7055). CECT 7055 was used to transform potato plants according to conventional protocols of transformation of this species (41)

b. Plants Constitutively Expressing glgP and Possessing a High Cytosolic GP Activity.

Figure 3:
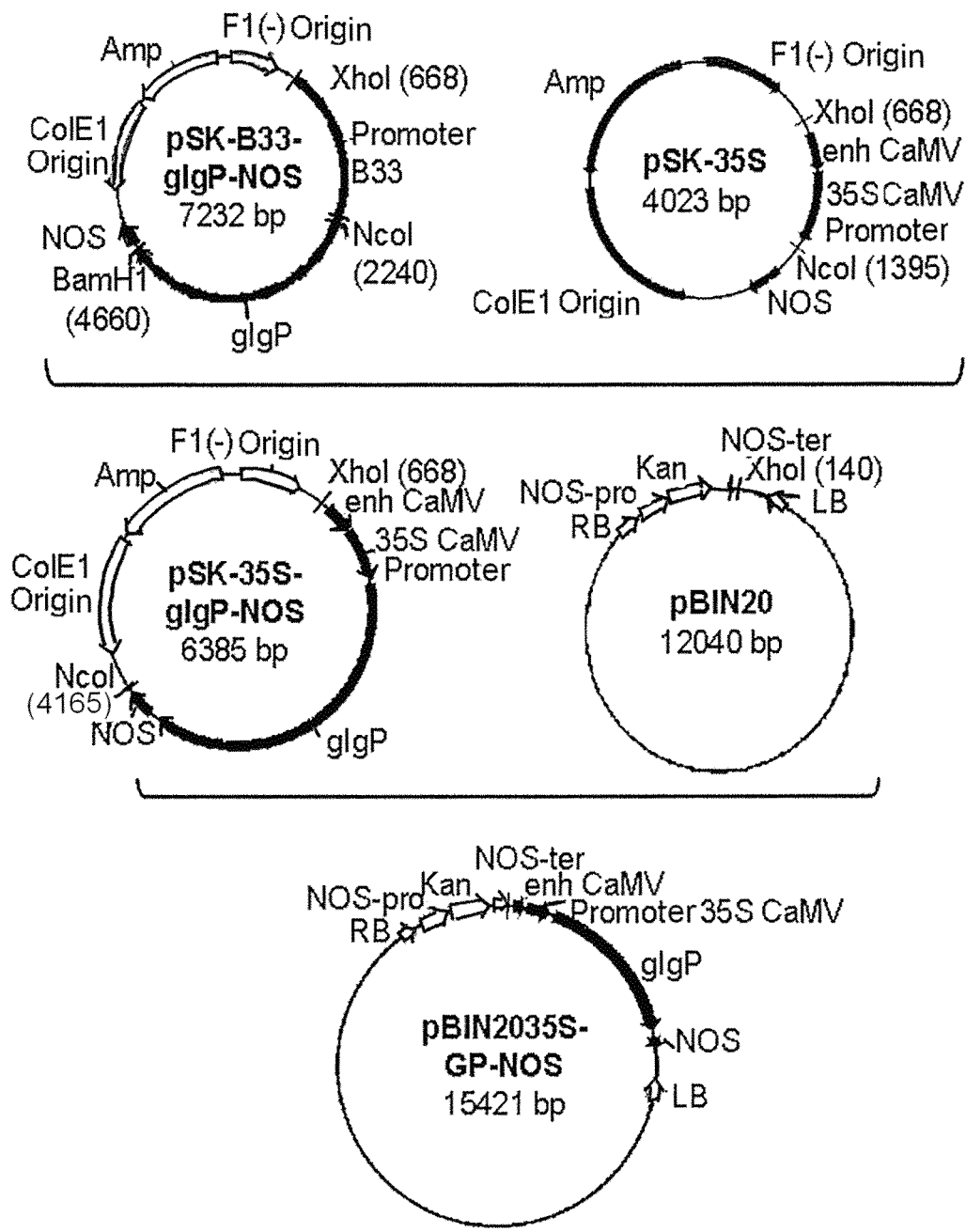
FIG. 3: Stages of construction of expression plasmid pBIN2035S-GP-NOS.

For the production of plants with high cytosolic GP activity, *E. coli* glgP gene constructs were created whose expression is governed by the constitutive promoter 35S of the tobacco mosaic virus. For this, the plasmid pSK-35S was digested with XhoI and NcoI. The released fragment (containing the promoter 35S attached to a booster region (42), was cloned between XhoI and NcoI sites of plasmid pSK-B33-glgP-NOS, resulting in the plasmid pSK-35S-glgP-NOS (FIG. 3). In order to transfer this construction to the plant genome via *A. tumefaciens*, it must previously be cloned in a binary plasmid. To do this, pSK-35S-glgP-NOS was digested sequentially with enzymes NotI, T4 DNA polymerase and XhoI. The fragment released was cloned into the binary plasmid pBIN20 which had previously been digested successively with the enzymes HpaI, T4 DNA polymerase and XhoI. The plasmid thus obtained was designated by the name of pBIN2035S-GP-NOS (FIG. 3). PBIN2035S-GP-NOS was introduced by electroporation into different strains of *A. tumefaciens* (such as strain C58:GV2260 with the deposit number CECT 7054) necessary to transform species such as potato, *Arabidopsis thaliana*, tomato, tobacco, corn and rice.

Thus, the first object of the present invention relates to a method for obtaining transgenic plants with high GP activity, high starch content and yield and a high amylose/amylopectin ratio, with respect to the untransformed wild plants, characterized by transformation of the wild plant with an expression vector comprising a nucleotide sequence of animal, plant or bacterial origin, which is encoded for a protein with high GP activity and is expressed within the transformed plant.

In a preferred embodiment, the method of the invention is characterized in that the GP activity of the protein encoded and expressed within the transformed plant is at least 5 times the GP activity of the wild plant, the starch content of transgenic plants produced is at least 20% higher than in wild plants and the value of amylose content in transgenic plants produced is at least 10% higher than the value of the amylose content of untransformed wild plants in all cases, grown under the same conditions as the transgenic plants.

In another preferred embodiment, the method of the invention is characterized in that the nucleotide sequence within the expression vector used to transform the wild plant is selected from:
  a. A nucleotide sequence coding for the amino acid sequence characterized by SEQ ID NO:4;
  b. A nucleotide sequence characterized by SEQ ID NO:3;
  c. A nucleotide sequence that hybridizes with those defined in "a" or "b" and encodes for an enzyme product with GP activity;
  d. A nucleotide sequence that differs from those in "a", "b" or "c" due to the degeneracy of the genetic code.

In another preferred embodiment, the method of the invention is characterized in that the high GP activity in the transformed transgenic plant can be achieved both at a cytosolic level, by transforming the wild plant with *Agrobacterium tumefaciens* CECT 7054 which comprises the plasmidpBIN2035S-GP-NOS, and at a plastidial level, by transforming the wild plant with *Agrobacterium tumefaciens* CECT 7055 which comprises the plasmid pBIN20-B33-C1P-GP-NOS.

The second aspect of the present invention relates to the expression vectors:
  *Agrobacterium tumefaciens* CECT 7054 characterized by comprising the plasmid pBIN2035S-GP-NOS
  *Agrobacterium tumefaciens* CECT 7055 characterized by comprising the plasmid pBIN20-B33-C1P-GP-NOS.

The third object of the present invention relates to cells transformed or infected with the two vectors mentioned above, characterized by being a bacterial or plant cell.

In a preferred embodiment, the bacterial cell of the invention is characterized as a bacterial cell of *E. coli* BL21 (DE3) C43, transformed with plasmid pET15b-glgP expressing the gene encoding the recombinant GP protein.

In another preferred embodiment, the plant cell of the invention is characterized by being transformed or infected by *Agrobacterium tumefaciens* CECT 7054 which comprises the plasmid pBIN2035S-GP-NOS or by *Agrobacterium tumefaciens* CECT 7055 which comprises the plasmid pBIN20-B33-C1P-GP-NOS, and by belonging, among others, to any of the following plant species: potato (*Solanum tuberosum*), tobacco (*Nicotiana tabacum*), rice (*Oryza sativa*), corn (*Zea mays*) and arabidopsis (*Arabidopsis thaliana*).

The fourth object of the present invention relates to the use of the previously defined bacterial cell to produce active recombinant GP protein, and the production of specific antibodies against GP.

The fifth object of the present invention relates to the use of bacterial or plant cells transformed or infected with *Agrobacterium tumefaciens* CECT 7054 which comprises the plasmid pBIN2035S-GP-NOS or with *Agrobacterium tumefaciens* CECT 7055 which comprises the plasmid pBIN20-B33-C1P-GP-NOS, for the production of starch.

The sixth object of the present invention relates to transgenic plants transformed with vector *Agrobacterium tumefaciens* CECT 7054 comprising the plasmid pBIN2035S-GP-NOS or with *Agrobacterium tumefaciens* CECT 7055 which comprises the plasmid pBIN20-B33-C1P-GP-NOS and that are characterized by high GP activity as regards to the wild plant, both at cytosolic and plastidial levels and, consequently, a high starch content and yield and a high amylose/amylopectin ratio compared to the untransformed wild plant, in all cases, grown under the same conditions and at the same time of year as the transgenic plants.

In a preferred embodiment, the transgenic plant of the invention is characterized in that GP activity is at least 5 times the GP activity of the wild plant, its starch content is at least 20% higher than the starch content of wild plants and the amylose content value is at least 10% higher than the amylose content value of the wild plants, cultivated in all cases under the same conditions.

In another preferred embodiment, the transgenic plant of the invention is characterized in that it expresses the glgP gene (SEQ ID NO: 3) and encodes for proteins with high GP activity, and furthermore, is selected from the group comprising: potato (*Solanum tuberosum*), tobacco (*Nicotiana tabacum*), rice (*Oryza sativa*), corn (*Zea mays*) and arabidopsis (*Arabidopsis thaliana*).

The seventh object of the present invention relates to the use of the aforementioned transgenic plants for the production of starch.

The eighth object of the present invention relates to polyclonal or monoclonal antibodies against the GP enzyme.

The ninth object of the present invention relates to the use of said antibodies to measure the GP concentration present in a sample.

DEPOSIT OF MICROORGANISMS UNDER THE BUDAPEST TREATY

The microorganisms used in the present invention were deposited in the Spanish Type Culture Collection (Colección Españiola de Cultivos Tipo—CECT), located at the Research Building of Valencia University, Burjassot Campus, Burjassot 46100 (Valencia, Spain).
  Strain of *E. coli* BL21 (DE3) C43 transformed with plasmid pET15b-glgP, deposited on 7 Mar. 2005 under deposit number CECT 7071, in accordance with the Budapest Treaty.
  Strain of *A. tumefaciens* C58: GV2260 transformed with the plasmid pBIN20-B33-C1P-GP-NOS, deposited on 14 Jan. 2005 under deposit number CECT 7055, in accordance with the Budapest Treaty.
  Strain of *A. tumefaciens* C58: GV2260 transformed with the plasmid pBIN2035S-GP-NOS, deposited on 14 Jan. 2005 under deposit number CECT 7054, in accordance with the Budapest Treaty.

EXAMPLES

The examples presented below are intended to illustrate the invention without limiting the scope thereof.

Example 1

Production in *Escherichia coli* of a Recombinant GP

Knowledge of the nucleotide sequence of the glgP gene coding for the GP of *E. coli* allowed the creation of two specific primers whose sequences are in sense 5'-3', SEQ ID NO: 1 and SEQ ID NO: 2. By using these primers, a DNA fragment from genomic DNA of *E. coli* was amplified by conventional PCR methods; it was introduced into the plasmid pGemT-easy (Promega), resulting in the plasmid pG-glgP. PG-glgP was digested with restriction enzymes XhoI and BamHI. The fragment released (containing glgP) was cloned into the same restriction sites of the expression plasmid pET-15b (+) (Novagen). The resulting plasmid (designated by the name of pET15b-glgP, FIG. 1) was introduced by electroporation into *E. coli* BL21 (DE3) C43 (Novagen). The nucleotide sequence of the fragment cloned in pET-15b (+) is SEQ ID NO: 3. The deduced amino acid sequence after expression of SEQ ID NO: 3 is SEQ ID NO: 4.

Figure 4:
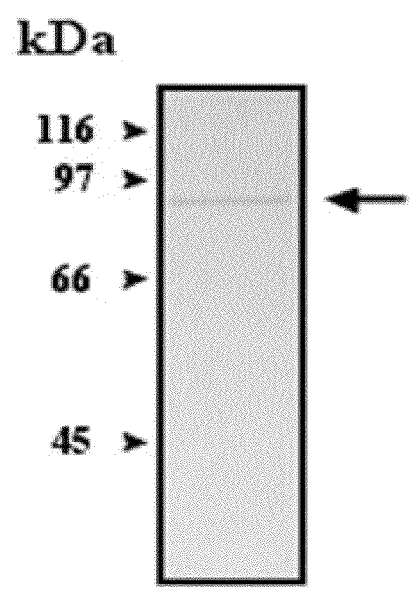
FIG. 4: SDS-PAGE. Staining of the recombinant GP purified from cell extracts of *E. coli* BL21 (DE3) C43 transformed with pET15b-glgP (CECT 7071).

The induction of the expression of glgP in bacteria BL21 (DE3) C43 transformed with pET15b-glgP (CECT 7071) occurred on adding 1 mM IPTG. After six additional hours of culture at 37° C., it was observed that bacteria transformed with pET15b-glgP accumulated a protein of approximately 95 kDa which could be purified to homogeneity in a simple way by means of affinity chromatography using the "His-bind" purification kit (Novagen) (FIG. 4). Moreover, these bacteria are characterized by having no glycogen (22).

Example 2

Enzymatic Assays

The enzymatic reactions were carried out at 37° C. GP activities were measured in the sense of the analysed polyglucan degradation. In a first step, 50 µL of reaction mixture consisting of 50 mM HEPES (pH 7.5), 30 mM phosphate buffer (pH 7.5), polyglucan (equivalent to 10 mM glucose) and protein extract, were incubated for 15 minutes. The reaction was stopped after boiling for 2 minutes and centrifuging at 30,000 g for 20 minutes. The existing released G1P in the supernatant was determined by any of the following methods:

By spectrophotometry. 300 µL of mixture containing Hepes 50 mM pH 7, EDTA 1 mM, $MgCl_2$ 2 mM, KCl 15 mM, $NAD^+$ 0.6 mM, a unit of phosphoglucomutase and another of glucose-6-phosphate dehydrogenase of *Leuconostoc mesenteroides*, and 30 µL of supernatant resulting from step one were incubated for 20 minutes. The production of NADH was monitored at 340 nm using a Multiskan EX spectrophotometer (Labsystems). The amount of NADH produced by any protein extract was negligible in the absence of glycogen in step one.

By chromatography. 40 µL of the supernatant from step 1 were subjected to high affinity liquid chromatography using a DX-500 Dionex system fitted to a Carbo-Pac PA10 column and amperometric detection.

The unit (U) is defined as the amount of enzyme that catalyzes the production of 1 µmol of product per minute.

Example 3

Identification of the Product with GP Activity

The product with GP activity thus obtained meets the general characteristics described in the scientific literature relating to any GP (22.43-45).

The GP of *E. coli* recognizes homopolysaccharides of 5 or more glucose molecules such as glycogen, starch, maltoheptaose, maltohexaose and maltopentaose.

It does not act on maltotetraose, maltotriose or maltose.

It is not to be inhibited by ADPglucose, UDPglucose, nucleoside mono-di- and tri-phosphates such as AMP, ADP and ATP, 3-phosphoglycerate, fructose-1,6-bisphosphate, fructose-6-phosphate, glucose-6-phosphate or glucose.

Apparent molecular weight of the purified protein in denaturing gels, about 93 kDa (FIG. 4).

Example 4

Figure 5:
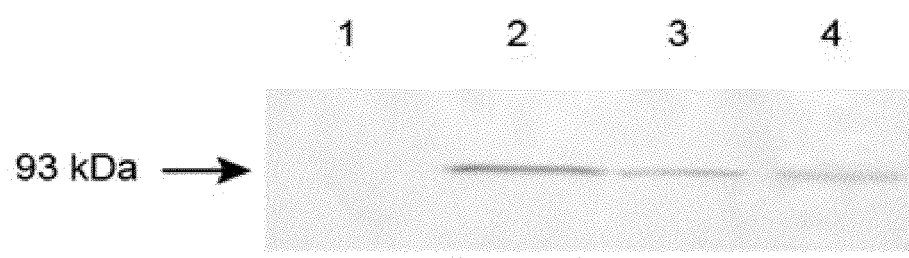
FIG. 5: Western blot of tubers of untransformed potato plants (line 1) and tubers from different clones of potato plants transformed with CECT 7054 (line 2) and CECT 7055 (lines 3 and 4). In each lane, 50 g of protein were loaded and were subjected to SDS-PAGE. The GP of *E. coli* was immunodecorated using the GP *E. coli* specific polyclonal antibody. Note that only lines expressing glgP of *E. coli* develop a band of approximately 93 kDa.

Preparation of Plants with High GP Activity (Both Plastidial and Cytosolic) Following Ectopic Expression of a Gene Coding for GP Using the strain of *A. tumefaciens* CECT 7054 (which houses the plasmid pBIN2035S-GP-NOS) the following were obtained: potato plants (*Solanum tuberosum*), tobacco (*Nicotiana tabacum*), rice (*Oryza sativa*), corn (*Zea mays*) and arabidopsis (*Arabidopsis thaliana*) constitutively expressing glgP. Using the strain of *A. tumefaciens* CECT 7055 (which houses the plasmid pBIN20-B33-CIP-GP-NOS), potato plants were obtained expressing glgP in their tubers. Tubers of potato plants transformed using CECT 7055 and/or CECT 7054 accumulated a protein that was specifically recognized by the polyclonal antibody obtained against the GP of *E. coli* (FIG. 5), however, the tubers of untransformed wild-type potato plants grown under the same environmental and farming conditions (irrigation, fertilizer, pesticide treatments, etc), and at the same time of year as the transformed plants, did not express this enzyme.

Figure 6:
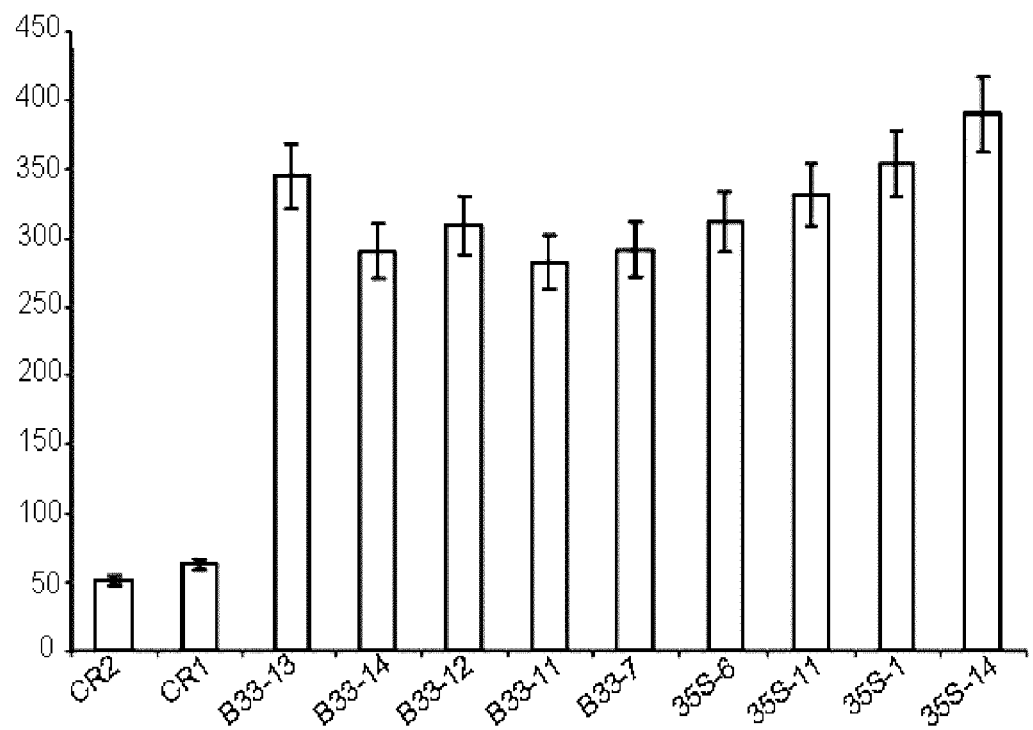
FIG. 6: GP activity in tubers of wild potato plants and potato plants expressing *E. coli* glgP after integrating into its genome constructions 355-glgP-NOS and B33-Ch1TP-glgP-NOS using strains of *A. tumefaciens* CECT 7054 and CECT 7055, respectively. The activity (in miliU/g fresh weight) refers to the amount of G1P produced from glycogen by fresh weight of a crude tuber extract. The two wild plants analyzed are designated as CR1 and CR2. Transgenic plants receive the designation of B33-7, B33-11, B33-12, B33-13 and B33-14 (those obtained using CECT 7055) and 35S-1, 35S-6, 35S-11 and 35S-14 (those obtained using CECT 7054). The values represented correspond to the standard average and deviation of tubers from 10 different plants per line.
Figure 7:
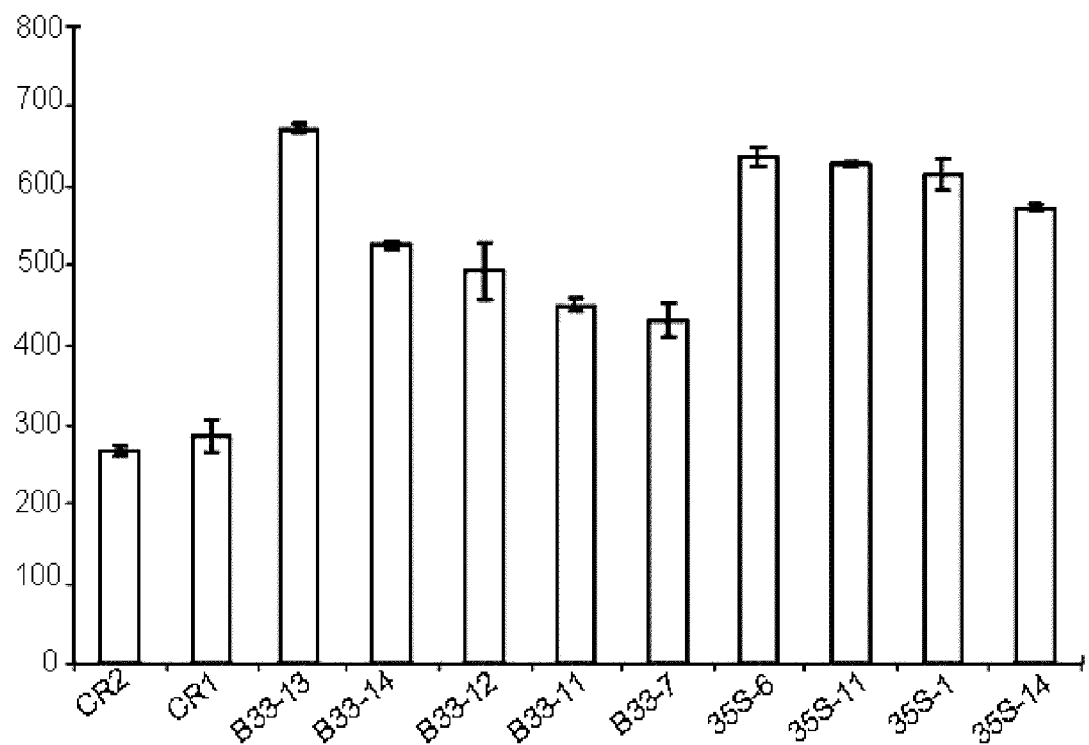
FIG. 7: Starch content in tubers of wild potato plants and potato plants expressing *E. coli* glgP after integration into its genome of constructions 355-glgP-NOS and B33-Ch1TP-glgP-NOS using strains of *A. tumefaciens* CECT 7054 and CECT 7055, respectively. The two wild plants analyzed are designated as CR1 and CR2. Transgenic plants receive the designation of B33-7, B33-11, B33-12, B33-13 and B33-14 (those obtained using CECT 7055) and 35S-1, 35S-6, 35S-11 and 35S-14 (those obtained using CECT 7054). The values represented correspond to the standard average and deviation of tubers from 10 different plants per line.

Both the tubers of transformed potato plants using CECT 7054 (which houses a construction that encodes for a GP located in the cytosol) and the transformed potato plants using CECT 7055 (which houses a construction that encodes a GP located in the amyloplasts) had the following characteristics:

1. GP activity is 5-8 times higher than that existing in untransformed tubers (FIG. 6), 2. High starch content compared to that in untransformed tubers (appr. 300 µmol glucose/g fresh weight compared to 450-700 µmol glucose/g fresh weight observed in lines 35S-glgP-NOS and B33-Ch1TP-glgP-NOS) (FIG. 7). Surprisingly, therefore, contrary to what happens in bacteria and mammalian cells, the increase in GP activity leads to an increase of starch content.

Figure 8A:
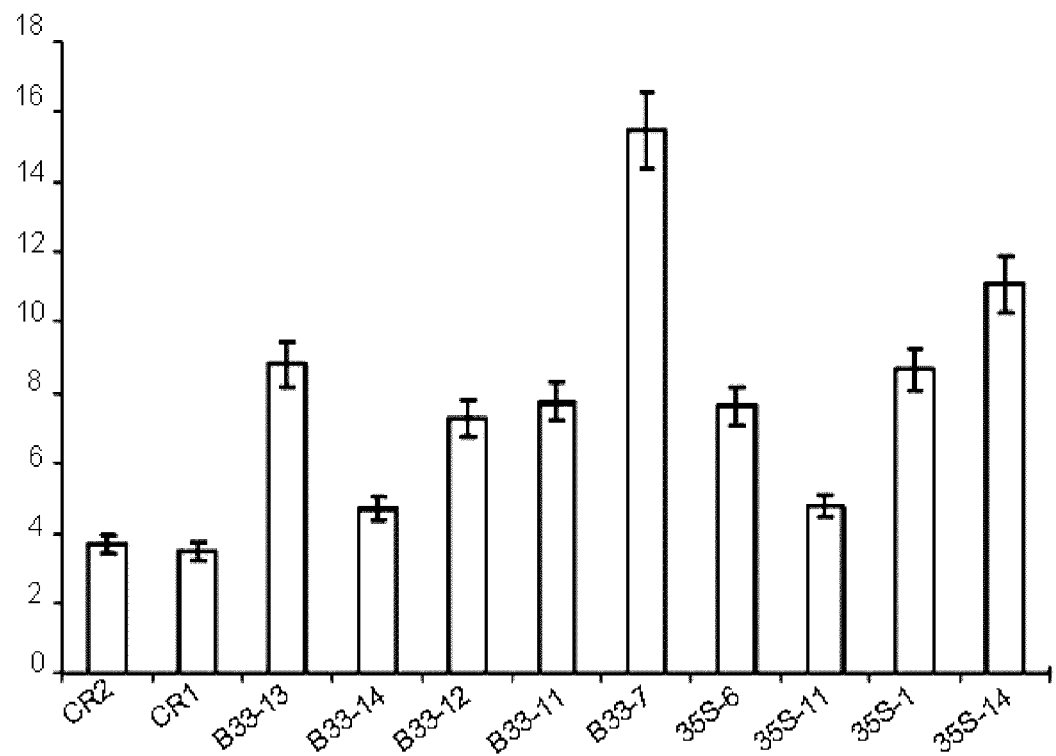
FIG. 8: Content of sucrose (A), glucose (B) and fructose (C) in tubers of wild potato plants and potato plants expressing *E. coli* glgP genome after integrating into their genome the constructions 35S-glgP-NOS and B33-Ch1TP-glgP-NOS using strains of *A. tumefaciens* CECT 7054 and CECT 7055, respectively. The two wild plants analyzed are designated as CR1 and CR2. Transgenic plants receive the designation of B33-7, B33-11, B33-12, B33-13 and B33-14 (those obtained using CECT 7055) and 35S-1, 35S-6, 35S-11 and 35S-14 (those obtained using CECT 7054). The values represented correspond to the standard average and deviation of tubers from 10 different plants per line
Figure 8B:
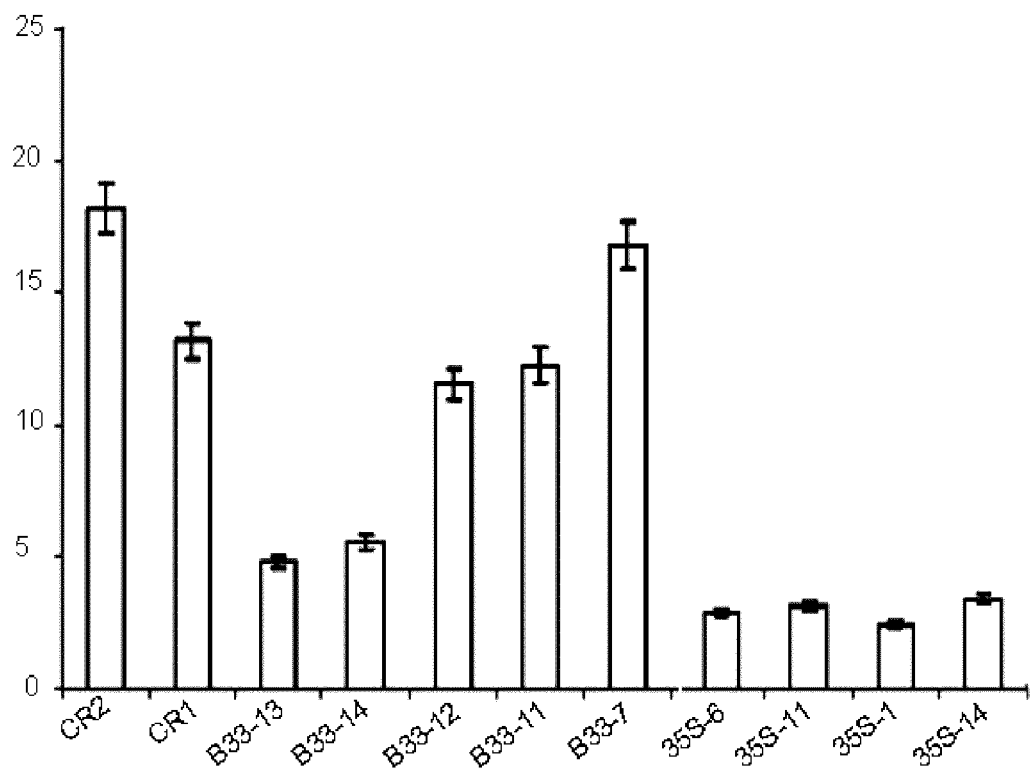
Figure 8C:
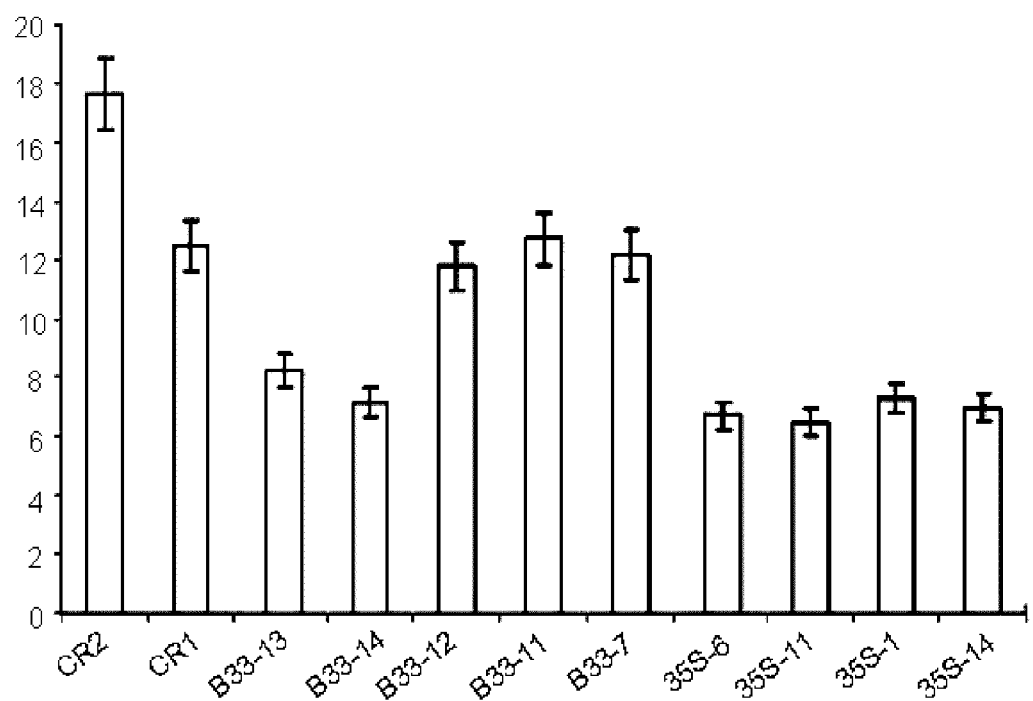
Figure 9:
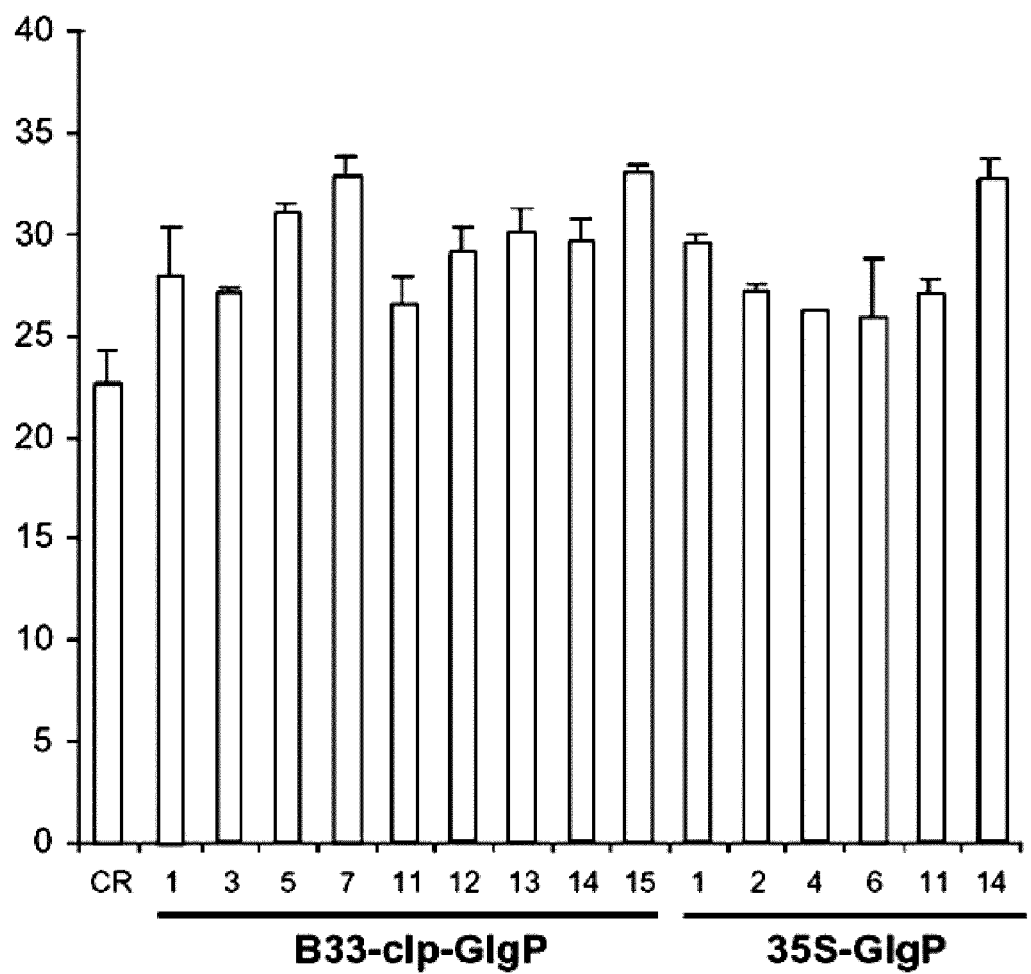
FIG. 9: The amylose/amylopectin ratio, expressed as % amylose in potato tubers of wild potato plants and potato plants expressing *E. coli* glgP after integrating into their genome the constructions 35S-glgP-NOS and B33-Ch1TP-glgP-NOS using strains of *A. tumefaciens* CECT 7054 and CECT 7055, respectively. The two wild plants analyzed are designated as CR1 and CR2. The transgenic plants receive the designation of B33-7, B33-11, B33-12, B33-13 and B33-14 (those obtained using CECT 7055) and 35S-1, 35S-6, 35S-11 and 35S-14 (those obtained using CECT 7054). The values represented correspond to the standard average and deviation of tubers from 10 different plants per line

3. High sucrose content and a tendency for low glucose and fructose (FIG. 8),

4. High amylose/amylopectin ratio compared with tubers of untransformed plants (FIG. 9). Again, this result is surprising because, if the GP had a degrading role of glucose polymers, the amylose/amylopectin ratio of tubers ectopically expressing GP should be lower than that observed in tubers of untransformed plants. Results illustrated in FIG. 7 and FIG. 9 indicate that the expression of GP leads to an increase in the amount of starch accumulated in the reserve organ.

5. The external morphology of plants ectopically expressing GP is not aberrant, after being compared with that of untransformed plants.

6. The number of tubers in lines ectopically expressing GP is normal when compared with untransformed plants. Productivity in kg fresh weight per plant is not affected by the expression of GP, but the starch production per plant is.

TABLE 1

Substrate specificity of GP of E. coli.

| Substrate | G1P | Maltose | Maltotriose | Maltotetraose | Maltopentaose | Maltohexose | Maltoheptose | Glycogen |
|---|---|---|---|---|---|---|---|---|
| Glycogen | 0.5 mM | b.d.l. | b.d.l. | b.d.l. | b.d.l. | b.d.l. | b.d.l. | 4.5 mM |
| Maltoheptose | 2.1 mM | b.d.l. | b.d.l. | 0.2 mM | 0.4 mM | 1 mM | 1.3 mM | — |
| Maltohexose | 1.7 mM | b.d.l. | b.d.l. | 0.6 mM | 0.5 mM | 2.1 mM | 0.1 | — |
| Maltopentaose | 1.6 mM | b.d.l. | b.d.l. | 1.0 mM | 2.2 mM | 0.2 | b.d.l. | — |
| Maltotetraose | b.d.l. | b.d.l. | b.d.l. | 5 mM | — | — | — | |
| Maltotriose | b.d.l. | b.d.l. | 5 mM | — | — | — | — | |
| Maltose | b.d.l. | 5 mM | — | — | — | — | — | |

The reaction mixture (50 µl) is composed of 50 mM HEPES (pH 7.5), 30 mM Pi, the glucan indicated (5 mM glucose) and 3 U of recombinant GP. After 3 hours of incubation at 37° C., the reaction was stopped after heating at 100° C. for 2 min. The products were analyzed by HPLC with amperometric detection

TABLE 2

Effect of different compounds on the GP activity of E. coli.

| Effectors | Activity (U/mg protein) | % control |
|---|---|---|
| None | 8.0 | 100 |
| ADPG, 2 mM | 8.3 | 104 |
| UDP glucose, 2 mM | 8.1 | 101 |
| AMP, 3 mM | 7.6 | 95 |
| ADP, 2 mM | 7.0 | 88 |
| ATP, 2 mM | 4.8 | 60 |
| Cyclic AMP, 1 mM | 7.3 | 91 |
| Pyrophosphate, 3 mM | 7.8 | 98 |
| 3-phosphoglycerate, 2 mM | 8.9 | 111 |
| Fructose-1,6-bisphosphate, 2 mM | 9.0 | 113 |
| Fructose-6-phosphate, 2 mM | 8.4 | 105 |
| Glucose-6-phosphate, 2 mM | 7.6 | 95 |
| Glucose, 20 mM | 7.2 | 90 |

BIBLIOGRAPHY

1. Okita, T. W (1992) Is there an alternative pathway for starch síntesis? Plant Physiol. 100, 560-56.
2. Müller-Röber, B., Sonnewald, U., Willmitzer, L. (1992) Inhibition of the ADP-glucose pyrophosphorylase in transgenic potatoes leads to sugar-storing tubers and influences tuber formation and expresiön of tuber storage protein genes. EMBO J. 11, 1229-1238.
3. Stark, D. M., Timmerman, K. P., Barry, G. F., Preiss, J., Kishore, G. M. (1992) Regulation of the amount of starch in plant fishes by ADPglucose pyrophosphorylase. Science 258, 287-282.
4. Neuhaus, E. H., Häusler, R. E., Sonnewald, U. (2005) No time to shift the paradigm on the metabolic pathway to transitory starch in leaves. Trends Plant Sci. 10, 154-156.
5. Murata, T., Sugiyama, T., Minamikawa, T., Akazawa, T. (1966) Enzymic mechanism of starch synthesis in ripening rice grains. Mechanism of the sucrose-starch conversion. Arch. Biochem. Biophys. 113, 34-44.
6. Delmer, D. P. (1972) The purification and properties of sucrose synthase from etiolated Phaseolus aureus seedlings. J. Biol. Chem. 247, 3822-3828
7. Baroja-Fernández, E., Muñoz, F. J., Saikusa, T., Rodríguez-López, M., Akazawa, T., Pozueta-Romero, J. (2003) Sucrose synthase catalyzes the de novo production of ADPglucose linked to starch biosynthesis in heterotrophic tissues of plants. Plant Cell Physiol. 44, 500-509.
8. Muñoz, F. J., Baroja-Fernández, E., Morán-Zorzano, M. T., Viale, A. M., Etxeberria, E., Alonso-Casajús, N., Pozueta-Romero, J. (2005) Sucrose synthase controls the intracellular levels of ADPglucose linked to transitory starch biosynthesis in source leaves. Plant Cell Physiol. 46, 1366-1376.
9. Muñoz, F. J., Morán-Zorzano, M. T., Alonso-Casajús, N., Baroja-Fernández, E., Etxeberria, E., Pozueta-Romero, J. (2006) New enzymes, new pathways and an alternative view on starch biosynthesis in both photosynthetic and heterotrophic tissues of plants. Biocatal. Biotransformation 24, 63-76.
10. Rodríguez-López, M., Baroja-Fernández, E., Zandueta-Criado, A., Pozueta-Romero, J. (2000) "Adenosine diphosphate glucose pyrophosphatase: a plastidial phosphodiesterase that prevents starch biosynthesis". Proc. Natl. Acad. Sci., 97, 8705-8710.
11. Baroja-Fernández, E., Zandueta-Criado, A., Rodríguez-López, M., Akazawa, T., Pozueta-Romero, J. (2000) "Distinct isoforms of ADPglucose pyrophosphatase and ADP-glucose pyrophosphorylase occur in the suspension-cultured cells of sycamore (Acer pseudoplatanus L.). FEBS Lett. 480, 277-282.
12. Muñoz, F. J., Baroja-Fernández, E., Alonso-Casajús, N., Morán-Zorzano, M. T., Pozueta-Romero, J. (2006) Cloning, expression and characterization of a Nudix hydrolase that catalyzes the hydrolytic breakdown of ADP-glucose linked to starch biosynthesis in Arabidopsis thaliana. Plant Cell Physiol. 47, 926-934.
13. Nanjo, Y., Oka, H., Ikarashi, N., Kanedo, K., Kitajima, A., Mitsui, T., Muñoz, F. J., Rodríguez-López, M., Baroja-Fernández, E., Pozueta-Romero, J. (2006) Cloning, expression and characterization of a N-glycosylated plastidial nucleotide pyrophosphatase/phosphodiesterase. Plant Cell 18, 2582-2592; PCT/ES01/00021; PCT: ES03/00363; P200601235).
14. Moreno-Bruna, B., Baroja-Fernández, E., Muñoz, F. J., Bastarrica-Berasategui, A., Zandueta-Crido, A., Rodríguez-López, M., Lasa, I., Akazawa, T., Pozueta-Romero, J. (2001) "Adenosine diphosphate sugar pyrophosphatase prevents glycogen biosynthesis in Escherichia coli" Proc. Natl. Acad. Sci. 98, 8128-8132.
15. Morán-Zorzano, M. T., Viale, A. M., Muñoz, F. J., Alonso-Casajús, N., Eydallín, G. G., Zugasti, B., Baroja-Fernández, E., Pozueta-Romero, J. (2007) Escherichia coli AspP activity is enhanced by molecular crowding and by both glucose-1,6-bisphosphate and nucleotide-sugars. FEBS Lett. 581, 1035-1040.

16. Asatsuma, S., Sawada, C., Itoh, K., Okito, M., Kitajima, A., Mitsui, T. (2005) Involvement of □-amylase I-1 in starch degradation in rice amyloplasts. Plant Cell Physiol. 46, 858-869.
17. Smith, A. M., Zeeman, S. C., Smith, S. M. (2005) Starch degradation. Annu. Rev. Plant Biol. 56, 73-98.
18. Baqué, S., Guinovart, J. J., Gómez-Foix, A. M. (1996) Overexpression of muscle glycogen phosphorylase in cultured human muscle fibers causes increased glucose consumption and nonoxidative disposal. J. Biol. Chem. 271, 2594-2598.
19. Burwinkel, B., Bakker, H. D., Herschkovitz, E., Moses, S. W., Shin, Y. S., Kilimann, M. W. (1998) Mutations in the liver glycogen phosphorylase gene (PYGL) underlying glycogenosis type VI. Am. J. Hum. Genet. 62, 785-791.
20. Bollen, M., Keppens, S., Stalmans, W. (1998) Specific features of glycogen metabolism in the liver. Biochem. J. 336, 19-31.
21. Newgard, C. B., Hwang, P. K., Fletterick, R. J. (1989) The family of glycogen phosphorylases: structure and function. Crit. Rev. Biochem. Mol. Biol. 24, 69-99.
22. Alonso-Casajús, N., Dauvillée, D., Viale, A. M., Muñoz, F. J., Baroja-Fernández, E., Morán-Zorzano, M. T., Eydallin, G., Ball, S., Pozueta-Romero, J. (2006) Glycogen phosphorylase, the product of the glgP gene, catalyzes glycogen breakdown by removing glucose units from the nonreducing ends in *Escherichia coli*. J. Bacteriol. 188, 5266-5272.
23. Weise, S. E., Schrader, S. M., Kleinbeck, K. R., Sharkey, T. D. (2006) Carbon balance and circadian regulation of hydrolytic and phosphorolytic breakdown of transitory starch. Plant Physiol. 141, 879-886.
24. Duwenig, E., Steup, M., Willmitzer, L., Kossmann, J. (1997) Antisense inhibition of cytosolic phosphorylase in potato plants (*Solanum tuberosum* L.) affects tuber sprouting and flower formation with only little impact on carbohydrate metabolism. Plant J. 12, 323-333.
25. Schupp, N., Ziegler, P. (2004) The relation of starch phosphorylases to starch metabolism in wheat. Plant Cell Physiol. 45, 1471-1484.
26. Sonnewald, U., Basner, A., Greve, B., Steup, M. (1995) A second L-type esozyme of potato glucan phosphorylase: cloning, antisense inhibition and expression analysis. Plant Mol. Biol. 27, 567-576.
27. Zeeman, S. C., Thorneycroft, D., Schupp, N., Chapple, A., Weck, M., Dunstan, H., Haldimann, P., Bechtold, N., Smith, A. M., Smith, S. M. (2004) Plastidial alpha-glucan phosphorylase is not required for starch degradation in *Arabidopsis* leaves but has a role in the tolerance of abiotic stress. Plant Physiol. 135, 849-858.
28. Dauvillée, D., Chochois, V., Steup, M., Haebel, S., Eckermann, N., Ritte, G., Ral, J.-P., Colleoni, C., Hicks, G., Wattebled, F., Deschamps, P., d'Hulst, C., Liénard, L., Cournac, L., Putaux, J.-L., Dupeyre, D., Ball, S. G. (2006) Plastidial phosphorylase is required for normal starch synthesis in *Chlamydomonas reinhardtii*. Plant J. 48, 274-285.
29. St-Pierre, B., Brisson, N. (1995) Induction of the plastidic starch-phosphorylase gene in potato storage sink tissue. Planta 195, 339-344
30. Schupp, N., Ziegler, P. (2004) The relation of starch phosphorylases to starch metabolism in wheat. Plant Cell Physiol. 45, 1471-1484.
31. Schneider, E. M., Becker, J. U., Volkmann, D. (1981) Biochemical properties of potato phosphorylase change with its intracellular localization as revealed by immunological methods. Planta 151, 124-134.
32. Nakamura, Y., Yuki, K. (1992) Changes in enzyme activities associated with carbohydrate metabolism during the development of rice endosperm. Plant Sci. 82, 15-20.
33. Nelson, O., Pan, D. (1995) Starch synthesis in maize endosperms. Annu. Rev. Plant Physiol. Plant Mol. Biol. 46, 475-496.
34. Baroja-Fernández, E., Muñoz, F. J., Zandueta-Criado, A., Morán-Zorzano, M. T., Viale, A. M., Etxeberria, E., Alonso-Casajús, N., Pozueta-Romero, J. (2004) Most of ADPglucose linked to starch biosynthesis occurs outside the chloroplast in source leaves. Proc. Natl. Acad. Sci. USA. 101, 13080-13085.
35. Muñoz, F. J., Baroja-Fernández, E., Morán-Zorzano, M. T., Viale, A. M., Etxeberria, E., Alonso-Casajús, N., Pozueta-Romero, J. (2005) Sucrose synthase controls the intracellular levels of ADPglucose linked to transitory starch biosynthesis in source leaves Plant Cell Physiol. 2005 August; 46(8):1366-76.
36. Andersson, M., Melander, M., Pojmark, P., Larsson, H., Bülow, L, Hofvander, P. (2006) "Targeted gene supresión by RNA interference: an efficient method for production of high-amylose potato lines" J. Biotechnol. 123, 137-148.
37. Towbin, H., Staehelin, T., Gordon, J. (1979) "Electrophoretic transfer of proteins from polyacrylamide gels to nitrocellulose sheets: procedures and some applications" Proc. Natl. Acad. Sci. USA 76, 4350-4354.
38. Liu, X. J., Prat, S., Willmitzer, L. Frommer, W. B. (1990) Cis regulatory elements directing tuber-specific and sucrose-inducible expresión of a chimeric class I patatin promoter-GUS-gene fusion. Mol. Gen. Genetics 223, 401-406.
39. Houlné, G., Schantz, M-L., Meyer, B., Pozueta-Romero, J., Schantz, R. (1994) "A chromoplast-specific protein in *Capsicum annuum*: characterization and expression of the corresponding gene" Curr. Genet. 26, 524-527.
40. Hennegan, K. P., Danna, K. J. (1998) pBIN20: An improved binary vector for *Agrobacterium*-mediated transformation. Plant Mol. Biol. Rep. 16, 129-131.
41. Rocha-Sosa, M., Sonnewald, U., Frommer, W., Stratmann, M., Schell, J., Willmitzer, L. (1989) Both developmental and metabolic signals activate the promoter of a class I patatine gene. EMBO J. 8, 23-29.
42. Gallie, D. R., Sleat, D. E., Watts, J. W., Turner, P. C., Wilson, T-MA. (1987) The 5'-leader sequence of tobacco mosaic virus RNA enhances the expression of foreign gene transcripts in vitro and in vivo. Nucleic Acids Res. 15, 3257-3273.
43. Schinzel, R., Nidetzky, B. (1999) Bacterial β-glucan phosphorylases. FEMS Microbiol. Lett. 171, 73-79.
44. Yu, F., Jen, Y., Takeuchi, E., Inouye, M., Nakayama, H., Tagaya, M., Fukui, T. (1988) β-glucan phosphorylase from *Escherichia coli*. J. Biol. Chem. 263, 13706-13711.
45. Buchbinder, J. L., Rath, V. L., Fletterick, R. J. (2001) Structural relationships among regulated and unregulated phosphorylases. Annu. Rev. Biophys. Biomol. Struct. 30, 191-209.

The invention claimed is:

1. A vector selected from the group consisting of *Agrobacterium tumefaciens* CECT 7054 characterized by comprising plasmid pBIN2035S-GP-NOS, or *Agrobacterium tumefaciens* CECT 7055 characterized by comprising plasmid pBIN20-B33-C1P-GP-NOS.

2. A process for obtaining transgenic plants with a high glucan phosphorylase (GP) activity, high starch content and yield, and/or a high amylose/amylopectin ratio, with respect to untransformed wild-type plants, characterized by the transformation of the wild-type plant with a vector comprising a nucleotide sequence of animal, plant or bacteria origin, said nucleotide sequence encoding and overexpressing for a protein with high GP activity characterized in that the nucleotide sequence comprised in the vector used to transform the wild-type plant is selected from the group consisting of:
   a. A nucleotide sequence encoding for the amino acid sequence characterized by SEQ ID NO: 4;
   b. A nucleotide sequence characterized by SEQ ID NO: 3;
   c. And a nucleotide sequence that differs from those in "a" or "b" due to the degeneracy of the genetic code.

3. A process for obtaining transgenic plants with a high glucan phosphorylase (GP) activity, high starch content and yield, and/or a high amylose/amylopectin ratio, with respect to untransformed wild-type plants, characterized by the transformation of the wild-type plant with a vector comprising a nucleotide sequence of animal, plant or bacteria origin, said nucleotide sequence encoding and overexpressing for a protein with high GP activity characterized in that the nucleotide sequence comprised in the vector, which encodes and overexpresses for a protein with glucan phosphorylase activity is the nucleotide sequence of glgP gene (SEQ ID NO: 3).

4. The process according to claim 2, wherein the high GP activity can be achieved by transforming the wild-type plants with the vector selected from the group consisting of: *Agrobacterium tumefaciens* CECT 7054 which comprises the plasmid pBIN2035S-GP-NOS, and *Agrobacterium tumefaciens* CECT 7055 which comprises the plasmid pBIN20-B33-C1P-GP-NOS.

5. A transgenic plant characterized by comprising a nucleotide sequence of animal, plant or bacterial origin, which encodes and overexpresses for a protein with high glucan phosphorylase (GP) activity, said transgenic plant being further characterized by having a high glucan phosphorylase activity compared to the wild-type plant, at both cytosolic and/or plastidial levels and, consequently, a high starch content and yield and/or a high amylose/amylopectin ratio, wherein the protein with high glucan phosphorylase activity is represented by SEQ ID No. 4.

6. A transgenic plant characterized by comprising a nucleotide sequence of animal, plant or bacterial origin, which encodes and overexpresses for a protein with high glucan phosphorylase (GP) activity, said transgenic plant being further characterized by having a high glucan phosphorylase activity compared to the wild-type plant, at both cytosolic and/or plastidial levels and, consequently, a high starch content and yield and/or a high amylose/amylopectin ratio, characterized by having been transformed with a vector consisting of *Agrobacterium tumefaciens* CECT 7054 which comprises the plasmid pBIN2035S-GP-NOS or of *Agrobacterium tumefaciens* CECT 7055 which comprises the plasmid pBIN20-B33-C1P-GP-NOS.

7. The transgenic plant according to claim 5, characterized by having either a GP activity at least 5 times the GP activity of the untransformed wild-type plant, or a starch content at least 20% higher than the starch content of untransformed wild-type plants, or an amylose content at least 10% higher than the amylose content of untransformed wild-type plants.

8. The transgenic plant according to claim 5, characterized in that the nucleotide sequence which encodes and overexpresses for a protein with glucan phosphorylase activity is the nucleotide sequence of glgP gene (SEQ ID NO: 3).

9. The transgenic plant according to claim 5, selected from the group consisting of: potato (*Solanum tuberosum*), tobacco (*Nicotiana tabacum*), rice (*Oryza sativa*), corn (*Zea mays*) and arabidopsis (*Arabidopsis thaliana*).

10. A plant cell, seed, or tuber from a transgenic plant according to claim 5.

11. The process according to claim 2, characterized in that the GP activity of the protein encoded and overexpressed within the transformed plant is at least 5 times the GP activity of the untransformed wild-type plant, the starch content is at least 20% higher than the starch content of untransformed wild-type plants, or the amylose content at least 10% higher than the amylose content of untransformed wild-type plants.

12. The transgenic plant of claim 5, wherein the nucleotide sequence that encodes and overexpresses for the protein with high glucan phosphorylase (GP) activity comprises a nucleotide sequence selected from the group consisting of SEQ ID NO: 3 and a nucleotide sequence differing from SEQ ID NO: 3 based on the degeneracy of the genetic code.

\* \* \* \* \*

SEQUENCE LISTING

<160> NUMBER OF SEQ ID NOS: 4

<210> SEQ ID NO 1
<211> LENGTH: 43
<212> TYPE: DNA
<213> ORGANISM: Escherichia coli

<400> SEQUENCE: 1
gctagcagga gctcgagtcc atgaatgctc cgtttacata ttc         43

<210> SEQ ID NO 2
<211> LENGTH: 31
<212> TYPE: DNA
<213> ORGANISM: Escherichia coli

<400> SEQUENCE: 2
ggatccttac aatctcaccg gatcgatatg c               31

<210> SEQ ID NO 3
<211> LENGTH: 2448
<212> TYPE: DNA
<213> ORGANISM: Escherichia coli

<400> SEQUENCE: 3

| | | | | | |
|---|---|---|---|---|---|
| atggatgctc | cgtttacata | ttcatcgccc | acgcttagcg | tagaagctct | taagcactct | 60 |
| atcgcttaca | agctgatgtt | tacgattgga | aaggacccgg | tcgtcgccaa | taaacatgaa | 120 |
| tggctgaacg | caacgttatt | tgctgtgcgc | gatcgtctcg | tggagcgctg | gttacgttca | 180 |
| aaccgtgccc | agttgtcgca | agaaactcgt | caggtttact | acctgtcgat | ggagttttg | 240 |
| attggccgta | cgctctccaa | cgccatgttg | tcgctaggaa | tttacgaaga | tgtacagggc | 300 |
| gcactggaag | cgatggggtt | aaatctcgaa | gagctgattg | atgaagaaaa | tgacccaggc | 360 |
| ctcggtaacg | gtggcctggg | acgtctggcg | gcttgcttcc | ttgattctct | ggcgacgtta | 420 |
| gggttgccgg | ggcgcggtta | cggcatccgc | tatgactacg | gtatgttcaa | gcagaacatc | 480 |
| gttaacggta | gccagaaaga | gtcgccgac | tactggctgg | aatacggtaa | cccgtgggaa | 540 |
| ttcaaacgcc | acaacacgcg | ctataaagtc | cgttttggcg | gtcgcattca | gcaggaaggt | 600 |
| aaaaaaacgc | gctggattga | aaccgaagag | attctgggag | tcgcttacga | tcagataatc | 660 |
| cctggttacg | acaccgacgc | gaccaacacg | ctgcgtttgt | ggagtgcgca | agccagtagc | 720 |
| gaaattaacc | tcggtaaatt | caaccagggt | gactacttcg | cggcagtgga | agataaaaac | 780 |
| cactccgaga | acgtatctcg | cgtactgtat | ccggatgact | ccacctactc | cgggcgtgac | 840 |
| gtgcgcctgc | gtcaggaata | cttcctggtt | tcctcgacca | ttcaggacat | tttaagccgc | 900 |
| cattatcagt | tgcataaaac | ctacgataac | ctggcggata | aaatcgcgat | tcatctcaat | 960 |
| gatacccatc | cggtactgtc | gattcctgag | atgatgcgtc | tgctgatcga | tgagcaccaa | 1020 |
| tttagctggg | acgacgcgtt | tgaggtgtgt | tgtcaggtct | tctcctacac | taaccacacg | 1080 |
| ctgatgagcg | aggcgctgga | aacctggccg | gttgatatgc | tgggtaaaat | tctgccgcgt | 1140 |
| cacctgcaga | tcatctttga | aatcaacgac | tatttcctga | aaaccttgca | ggaacagtat | 1200 |
| ccgaacgata | ccgatctgct | gggacgggcg | tcgatcattg | atgaatccaa | cggtcgtcgt | 1260 |
| gtgcgtatgg | cctggctggc | ggttgttgtg | agccacaaag | ttaacggtgt | atcggaactg | 1320 |
| cactctaatc | tgatggtgca | atcgttgttt | gccgactttg | cgaaaatctt | cccgggtcgt | 1380 |
| ttcaccaacg | tcaccaacgg | tgtgacgccg | cgtcgctggc | tggcggtagc | gaacccatcg | 1440 |
| cttttcagccg | tgctggacga | acacctgggc | cgtaactggc | gcaccgacct | tagcctgctt | 1500 |

```
aatgagctgc aacaacactg tgatttccca atggttaatc acgctgtgca tcaggcgaag    1560
ctggagaaca aaaagcgtct ggcagagtat atcgcccagc agctgaatgt ggtggtgaat    1620
ccaaaggcgt tgttcgatgt acaaatcaaa cgtattcacg aatacaaacg tcaattgatg    1680
aatgtgttgc atgtgattac ccgctataac cgcatcaagg ccgacccgga tgcgaagtgg    1740
gtaccgcgcg tgaatatttt tggcggtaag gcggcttcgg cctattacat ggcgaagcac    1800
attattcatt tgatcaatga cgtagcgaaa gtgatcaaca cgatccgca gattggcgat     1860 aagctgaaag tcgtgttcat cccgaactac agcgttagcc tggcgcagtt gatcattccg    1920
gcggcagatc tgtctgaaca gatttcgctg cagggacgg aagcttccgg caccagtaac     1980
atgaagtttg cgcttaacgg tgcgctgact atcggtacgt ggacggtgc gaatgtcgag     2040 atgctggatc atgtcggtgc tgacaatatc tttattttg gtaacacagc ggaagaagtg     2100
gaagaactgc gtcgtcaggg ctacaaaccg cgtgaatact acgagaaaga tgaggagctg    2160
catcaggtgc tgacgcaaat cggcagcggt gtattcagtc cggaagatcc gggtcgctat    2220
cgcgatctgg ttgattcgct gatcaacttc ggcgatcact accaggtact ggcggattat    2280
cgcagctatg tcgattgtca ggataaagtc gatgaactct acgagcttca ggaagagtgg    2340
accgcaaaag cgatgctgaa cattgccaat atgggctact tctcttctga ccgtactatc    2400
aaagagtacg ccgatcatat ctggcatatc gatccggtga gattgtaa              2448

<210> SEQ ID NO 4
<211> LENGTH: 815
<212> TYPE: PRT
<213> ORGANISM: Escherichia coli

<400> SEQUENCE: 4

Met Asp Ala Pro Phe Thr Tyr Ser Ser Pro Thr Leu Ser Val Glu Ala
1               5                   10                  15

Leu Lys His Ser Ile Ala Tyr Lys Leu Met Phe Thr Ile Gly Lys Asp
            20                  25                  30

Pro Val Val Ala Asn Lys His Glu Trp Leu Asn Ala Thr Leu Phe Ala
        35                  40                  45

Val Arg Asp Arg Leu Val Glu Arg Trp Leu Arg Ser Asn Arg Ala Gln
    50                  55                  60

Leu Ser Gln Glu Thr Arg Gln Val Tyr Tyr Leu Ser Met Glu Phe Leu
65                  70                  75                  80

Ile Gly Arg Thr Leu Ser Asn Ala Met Leu Ser Leu Gly Ile Tyr Glu
                85                  90                  95

Asp Val Gln Gly Ala Leu Glu Ala Met Gly Leu Asn Leu Glu Glu Leu
            100                 105                 110

Ile Asp Glu Glu Asn Asp Pro Gly Leu Gly Asn Gly Gly Leu Gly Arg
        115                 120                 125

Leu Ala Ala Cys Phe Leu Asp Ser Leu Ala Thr Leu Gly Leu Pro Gly
    130                 135                 140

Arg Gly Tyr Gly Ile Arg Tyr Asp Tyr Gly Met Phe Lys Gln Asn Ile
145                 150                 155                 160

Val Asn Gly Ser Gln Lys Glu Ser Pro Asp Tyr Trp Leu Glu Tyr Gly
                165                 170                 175

Asn Pro Trp Glu Phe Lys Arg His Asn Thr Arg Tyr Lys Val Arg Phe
            180                 185                 190

Gly Gly Arg Ile Gln Gln Glu Gly Lys Lys Thr Arg Trp Ile Glu Thr
        195                 200                 205
```

```
Glu Glu Ile Leu Gly Val Ala Tyr Asp Gln Ile Ile Pro Gly Tyr Asp
    210                 215                 220

Thr Asp Ala Thr Asn Thr Leu Arg Leu Trp Ser Ala Gln Ala Ser Ser
225                 230                 235                 240

Glu Ile Asn Leu Gly Lys Phe Asn Gln Gly Asp Tyr Phe Ala Ala Val
                245                 250                 255

Glu Asp Lys Asn His Ser Glu Asn Val Ser Arg Val Leu Tyr Pro Asp
            260                 265                 270

Asp Ser Thr Tyr Ser Gly Arg Asp Val Arg Leu Arg Gln Glu Tyr Phe
        275                 280                 285

Leu Val Ser Ser Thr Ile Gln Asp Ile Leu Ser Arg His Tyr Gln Leu
    290                 295                 300

His Lys Thr Tyr Asp Asn Leu Ala Asp Lys Ile Ala Ile His Leu Asn
305                 310                 315                 320

Asp Thr His Pro Val Leu Ser Ile Pro Glu Met Met Arg Leu Leu Ile
                325                 330                 335

Asp Glu His Gln Phe Ser Trp Asp Asp Ala Phe Glu Val Cys Cys Gln
            340                 345                 350

Val Phe Ser Tyr Thr Asn His Thr Leu Met Ser Glu Ala Leu Glu Thr
        355                 360                 365

Trp Pro Val Asp Met Leu Gly Lys Ile Leu Pro Arg His Leu Gln Ile
    370                 375                 380

Ile Phe Glu Ile Asn Asp Tyr Phe Leu Lys Thr Leu Gln Glu Gln Tyr
385                 390                 395                 400

Pro Asn Asp Thr Asp Leu Leu Gly Arg Ala Ser Ile Ile Asp Glu Ser
                405                 410                 415

Asn Gly Arg Arg Val Arg Met Ala Trp Leu Ala Val Val Ser His
            420                 425                 430

Lys Val Asn Gly Val Ser Glu Leu His Ser Asn Leu Met Val Gln Ser
        435                 440                 445

Leu Phe Ala Asp Phe Ala Lys Ile Phe Pro Gly Arg Phe Thr Asn Val
    450                 455                 460

Thr Asn Gly Val Thr Pro Arg Arg Trp Leu Ala Val Ala Asn Pro Ser
465                 470                 475                 480

Leu Ser Ala Val Leu Asp Glu His Leu Gly Arg Asn Trp Arg Thr Asp
                485                 490                 495

Leu Ser Leu Leu Asn Glu Leu Gln Gln His Cys Asp Phe Pro Met Val
            500                 505                 510

Asn His Ala Val His Gln Ala Lys Leu Glu Asn Lys Lys Arg Leu Ala
        515                 520                 525

Glu Tyr Ile Ala Gln Gln Leu Asn Val Val Asn Pro Lys Ala Leu
    530                 535                 540

Phe Asp Val Gln Ile Lys Arg Ile His Glu Tyr Lys Arg Gln Leu Met
545                 550                 555                 560

Asn Val Leu His Val Ile Thr Arg Tyr Asn Arg Ile Lys Ala Asp Pro
                565                 570                 575

Asp Ala Lys Trp Val Pro Arg Val Asn Ile Phe Gly Gly Lys Ala Ala
            580                 585                 590

Ser Ala Tyr Tyr Met Ala Lys His Ile Ile His Leu Ile Asn Asp Val
        595                 600                 605

Ala Lys Val Ile Asn Asn Asp Pro Gln Ile Gly Asp Lys Leu Lys Val
    610                 615                 620
```

-continued

```
Val Phe Ile Pro Asn Tyr Ser Val Ser Leu Ala Gln Leu Ile Ile Pro
625             630                 635                 640

Ala Ala Asp Leu Ser Glu Gln Ile Ser Leu Ala Gly Thr Glu Ala Ser
                645                 650                 655

Gly Thr Ser Asn Met Lys Phe Ala Leu Asn Gly Ala Leu Thr Ile Gly
            660                 665                 670

Thr Leu Asp Gly Ala Asn Val Glu Met Leu Asp His Val Gly Ala Asp
        675                 680                 685

Asn Ile Phe Ile Phe Gly Asn Thr Ala Glu Glu Val Glu Glu Leu Arg
    690                 695                 700

Arg Gln Gly Tyr Lys Pro Arg Glu Tyr Tyr Glu Lys Asp Glu Glu Leu
705             710                 715                 720

His Gln Val Leu Thr Gln Ile Gly Ser Gly Val Phe Ser Pro Glu Asp
                725                 730                 735

Pro Gly Arg Tyr Arg Asp Leu Val Asp Ser Leu Ile Asn Phe Gly Asp
            740                 745                 750

His Tyr Gln Val Leu Ala Asp Tyr Arg Ser Tyr Val Asp Cys Gln Asp
        755                 760                 765

Lys Val Asp Glu Leu Tyr Glu Leu Gln Glu Glu Trp Thr Ala Lys Ala
    770                 775                 780

Met Leu Asn Ile Ala Asn Met Gly Tyr Phe Ser Ser Asp Arg Thr Ile
785             790                 795                 800

Lys Glu Tyr Ala Asp His Ile Trp His Ile Asp Pro Val Arg Leu
                805                 810                 815
```